US012084357B2

(12) United States Patent
Baret (10) Patent No.: US 12,084,357 B2
(45) Date of Patent: Sep. 10, 2024

(54) AUTONOMOUS WATER ANALYSIS DEVICE AND SWIMMING POOL EQUIPPED WITH SUCH A DEVICE

(71) Applicant: BLEU ELECTRIQUE, Marseilles (FR)

(72) Inventor: Emmanuel Baret, Marseilles (FR)

(*) Notice: Subject to any disclaimer, the term of this patent is extended or adjusted under 35 U.S.C. 154(b) by 193 days.

(21) Appl. No.: 17/996,490

(22) PCT Filed: Apr. 20, 2021

(86) PCT No.: PCT/IB2021/053252
§ 371 (c)(1),
(2) Date: Oct. 18, 2022

(87) PCT Pub. No.: WO2021/214656
PCT Pub. Date: Oct. 28, 2021

(65) Prior Publication Data
US 2023/0219828 A1    Jul. 13, 2023

(30) Foreign Application Priority Data
Apr. 21, 2020 (FR) ...................... 2003981

(51) Int. Cl.
*C02F 1/00* (2023.01)
*C02F 103/42* (2006.01)

(52) U.S. Cl.
CPC .......... *C02F 1/001* (2013.01); *C02F 2103/42* (2013.01); *C02F 2201/001* (2013.01); *C02F 2201/009* (2013.01); *C02F 2209/003* (2013.01)

(58) Field of Classification Search
CPC ............................ C02F 1/001; C02F 2103/42; C02F 2201/001; C02F 2201/009; C02F 2209/003
(Continued)

(56) References Cited

U.S. PATENT DOCUMENTS 11,427,484 B1 *  8/2022  Reddy ................. C02F 1/46104
2010/0250449 A1   9/2010  Doyle et al.
(Continued)

FOREIGN PATENT DOCUMENTS

DE       20200900214 U1    6/2009

OTHER PUBLICATIONS

International Search Report for corresponding PCT/IB2021/053252 dated Jul. 20, 2021.
(Continued)

*Primary Examiner* — Huyen D Le
(74) *Attorney, Agent, or Firm* — Egbert, McDaniel & Swartz, PLLC (57) ABSTRACT

Disclosed is a device for analysing water and a swimming pool equipped with such a device. The device includes: an analysis chamber provided with at least one water inlet and at least one water outlet; a sealed housing adjacent to the analysis chamber and isolated from the analysis chamber by a partition; a data processor housed in the sealed housing; at least one probe electrically connected to a data input of the data processor; an electrical power supply electrically connected to a power input of the data processor, the electrical power supply having an electrical generator provided with a turbine housed in the analysis chamber, the electrical generator being electrically connected to the data input of the data processor. The device is useful for monitoring the sanitary state of the water of a swimming pool.

14 Claims, 5 Drawing Sheets

(58) Field of Classification Search
USPC .............................................................. 4/488
See application file for complete search history.

(56) References Cited

U.S. PATENT DOCUMENTS

| | | | |
|---|---|---|---|
| 2017/0226646 A1* | 8/2017 | Nourbakhsh | ....... C02F 1/46104 |
| 2017/0291141 A1* | 10/2017 | Dunham | ................ B01D 61/06 |
| 2017/0314282 A1* | 11/2017 | Nix | .......................... C02F 1/008 |
| 2018/0297862 A1 | 10/2018 | Nourbakhsh et al. | |
| 2021/0324649 A1* | 10/2021 | Revilla | ................. E04H 4/1209 |

OTHER PUBLICATIONS

Written Opinion of the International Searching Authority for corresponding PCT/IB2021/053252 dated Jul. 20, 2021.
Hoffman et al., "Energy Harvesting from Fluid Flow in Water Pipelines for Smart Metering Applications", J. Phys.: Conf. Ser. 476 012104, 2013.
International Preliminary Report on Patentability for corresponding PCT/IB2021/053252 dated Jul. 5, 2022.

* cited by examiner

ically be used for analyzing swimming pool water. More specifically, the device from the present invention is a device which aims to measure and transmit physical-chemical values of the water, such as temperature, turbidity, flow rate, pressure, pH or the like. It also relates to a swimming pool equipped with such device.

AUTONOMOUS WATER ANALYSIS DEVICE AND SWIMMING POOL EQUIPPED WITH SUCH A DEVICE

FIELD OF THE INVENTION

The present invention relates to an autonomous water analysis device that can in particular be used for analyzing swimming pool water. More specifically, the device from the present invention is a device which aims to measure and transmit physical-chemical values of the water, such as temperature, turbidity, flow rate, pressure, pH or the like. It also relates to a swimming pool equipped with such device.

The invention also has applications in verifying physical-chemical properties of water in a swimming pool and monitoring the sanitary quality and safety of the water.

The invention also has applications in the control of the members of a swimming pool filtration circuit.

DESCRIPTION OF RELATED ART

Guaranteeing the quality of the water in a swimming pool requires monitoring some number of physical-chemical parameters, such as the water temperature, potential-hydrogen (pH), the oxidation-reduction potential (ORP), the salinity (S) of the water, the total dissolved solids (TDS) and the turbidity of the water.

These parameters may be taken into consideration for driving a filtration circuit for the swimming pool or for controlling some equipment in an equipment room at the swimming pool, such as metering pumps, intended for supplying corrective additives to the water in the filtration circuit. This involves for example treatment products such as chlorine, bromine, active oxygen, or a liquid for pH correction.

The water analysis devices may be installed in the equipment room for the swimming pool and measure the parameters of the water passing through a pipe or branch of the water filtration circuit. They can be supplied with energy by an electric distribution grid or by an electric battery, either rechargeable or not.

Analysis and control devices are also known that are configured for floating on the water at the swimming pool. These devices are generally provided with a rechargeable battery for supplying them with electricity and also a transmitter-receiver for transmission of analysis data to equipment in the equipment room.

Document US 2018/0297862 describes a system for treatment of swimming pool water by electrolysis in order to disinfect the water. More specifically, the goal of the system is to regulate the production of a disinfectant. The system comprises a cylindrical enclosure arranged around an axis of revolution. The cylindrical enclosure houses an electrolytic treatment device, an electronic control device and a hydraulic generation device.

The cylindrical enclosure extends axially between the first end provided with a water inlet and a second end provided with a water outlet. Inside the cylindrical enclosure, the water circulates between the water inlet and the water outlet along of flow direction which is generally parallel to the axis of revolution. As a result of this, the electrolytic treatment device, the electronic control device and the hydraulic generation device are totally immersed in the water, which presents a risk relating to the seal necessary for the electronic control device and/or the hydraulic generation device.

The hydraulic generation device comprises a turbine intended to produce the electric energy needed for electrolysis of the water. But the sizing of this turbine, rotationally mobile around an axis of rotation which is parallel to the axis of revolution and in the flow direction of the water inside the cylindrical enclosure, does not serve to generate sufficient energy for electrolysis of the dirty water under the described conditions. The result of this is an unfitness to satisfy the operation thereof.

BRIEF SUMMARY OF THE INVENTION

The invention follows from the demonstration of some number of difficulties encountered with some number of known water analysis devices.

For water analysis devices supplied by an electric grid, a difficulty is associated with their connection to the grid and with the need to guarantee perfect electrical isolation of the connection from the liquid medium.

For autonomous water analysis devices comprising an electric generation device combining a turbine and a battery, it is generally desired to sustainably guarantee a complete seal for the electrical and/or electronic components making up the electric generation device and/or the battery against the water circulating inside the autonomous water analysis device.

A difficulty encountered with battery analysis devices is the durability of their operation. In fact, if the battery becomes discharged, verification of the sanitary quality of the water in the pool becomes uncertain or impossible. In addition, charging the battery also requires an electrical connection.

It follows from this that there is a need to have an autonomous water analysis device comprising an effective and efficient electric generation device for effectively charging the battery.

Another difficulty seen is an influence on the analysis and verification of the parameters of the water due to a possible failure of the filtration system. The filtration system failure may result, for example, from clogging of a filter, fouling of a pump, untimely closure of a valve or an obstruction of the skimmer. Such a failure may invalidate the measurement of the water parameters and prevent taking suitable corrective actions.

The goal of the present invention is to propose a water analysis device, and in particular for swimming pool water, which serves to avoid these difficulties.

In particular, the goal is to propose such an analysis device which is entirely independent, without any wire or electrical connection, and which does not require any human involvement for guaranteeing the continuity of its electric supply.

Another goal is to propose such an analysis device with which to detect and report as needed a filtration system failure for a swimming pool which is equipped with it.

Another goal is to propose such an analysis device which is simple and compact, in particular without a treatment device for the water, but whose function is to measure and transmit values of physical-chemical properties of the water, such as temperature, turbidity, flow rate, pressure, pH or the like, to a receiver in order to actuate another system, distinct from the analysis device.

Another goal of the invention is to propose a pool equipped with such an analysis device.

To achieve these goals, the invention proposes a water analysis device comprising:
an analysis chamber provided with at least one water inlet and at least one water outlet;

a sealed case which is adjacent to the analysis chamber and which is isolated from the analysis chamber via a partition;

a data processor housed in the sealed case;

at least one probe, electrically connected to a data input of he data processor, and extending into the analysis chamber;

an electric supply electrically connected to a supply input of the data processor, where the electric supply comprises an electric generator provided with a turbine housed in the analysis chamber, and where the electric generator delivers a signal that is a function of the rotation speed of the turbine and is electrically connected to the data input of the data processor for sending said signal to the data processor.

The analysis chamber may comprise a water inlet and a water outlet, provided as needed with connections for connecting the analysis chamber to the pipes of the water circuit. Additionally, the analysis chamber may be configured for reducing the flow rate of the water current which passes through it, in particular near the probe or probes. A reduced flow rate near the probe serves to guarantee a better reliability of the measurements in order to avoid disruptions which could be caused by a rapid movement of the water, such as cavitation or generation of static electricity. The reduction of the flow rate is local near the probes; it has no effect on the overall flow rate of the water passing through the analysis chamber.

The sealed case is adjacent to the analysis chamber and preferably secured with the analysis chamber. The sealed case may be formed from a single piece with the analysis chamber with a sealed partition for separation.

The sealed case overhangs the analysis chamber and is contiguous with the analysis chamber. In other words, the analysis chamber and the sealed case are laid out side-by-side with each other while being separated from each other by a partition shared by them.

The seal of the sealed case is understood mainly relative to the analysis chamber such that the water which fills the analysis chamber or which passes through the analysis chamber is not able to reach components housed in the sealed case. The sealed case may be sealed not only relative to the analysis chamber but also, and more generally, relative to the outside of the case. In this case, the seal serves to keep the components housed in the case protected from water and the ambient humidity.

The one or more probes of the device may be arranged entirely, or partially, in the analysis chamber in order to guarantee physical contact between the probes and the water filling the analysis chamber or passing through the analysis chamber.

The probe, or probes, may be selected from a temperature probe, a pH probe, an oxidation-reduction potential probe, a salinity probe, a total dissolved solids probe, an ammeter probe and a turbidity probe, for example.

The term "probe" is understood as any component or sensor sensitive to a chemical or physical property of the water, or of the water flow (pressure, flow rate, speed), and capable of delivering a signal which could be applied to the data input of the data processor. The signal can be applied directly to the data processor input in the case of a digital probe, or may be applied via an interface, comprising, for example one or more analog-digital converters and/or analog signal shaping stages (amplifier or other conditioning system).

The electric generator of the analysis device is supplied with energy by the turbine whose movement is caused by a flow of water passing through the analysis chamber. Electric generator is understood to mean any device with which to convert the mechanical energy of the turbine to electric energy. The electric generator may comprise, for example, one from a dynamo and an alternator. The electric energy provided by the electric generator serves to supply the data processor, the probes, and more generally all of the electrical or electronic components housed in the sealed case.

The turbine may comprise a propeller or blades arranged in the analysis chamber or portion of the analysis chamber through which a flow of water could pass.

The turbine may also be provided with a motor shaft connecting the propeller or blades thereof to the dynamo or the alternator of the electric generator, housed in the sealed case.

However, in order to avoid a motor shaft passing through a partition between the analysis chamber and the sealed case, the electric generator may comprise a permanent magnet inductor secured to the turbine and an armature housed in the sealed case. In this case, no mobile shaft or member passes through the partition and any risk of the failure of water-tightness may be avoided. The electric energy is produced by a magnetic coupling between the inductor and the armature through the partition which separates the analysis chamber from the sealed case.

According to an improvement, the electric supply may further comprise an electric energy storage unit housed inside the sealed case. For example, it involves a rechargeable battery.

The electric generator may also be connected to the energy storage unit, meaning the battery, so as to charge it and maintain the charge thereof.

The essential function of the battery is to guarantee the continuity of the operation of the analysis device, including in the temporary absence of water flow through the analysis chamber.

In the absence of water flow, the turbine is not driven and the electric generator delivers a diminished voltage and current. The null voltage applied at the data input of the data processor may then be used as a signal informing the data processor of a possible malfunction of a water filtration circuit for a swimming pool equipped with the analysis device. For example, it could be a circulation pump failure or clogging of a filter, which prevents the water from circulating. The data processor may then drive sending an alert signal or a command to trigger an alert signal. The data processor may also drive an inhibition of possible water correcting equipment. This way it is possible to avoid, for example, addition of a water correcting chemical agent to a pipe of the filtration circuit in which the water is not moving.

It is appropriate to indicate that the circulation pump is not necessarily running continuously. Thus, it is conceivable that an alarm is only issued when a malfunction of the circulation of water in the filtration circuit is detected while the pump is powered at the same time as detection of the malfunction. Running or stopping the pump may be information sent to the data processor by radio wave in the manner described later. An alert may also be issued when a malfunction of the water circulation, meaning no rotation of the turbine, is detected during some configurable time, for example 24 hours.

According to an advantageous possibility for implementation of the invention, the operation signal for the turbine rotation speed may be an output voltage from the electric generator. Since the voltage delivered by the electric generator is a function of the rotation speed of the turbine, it is also a function of the flow rate of water through the analysis chamber. The signal is then applied to the data input of the data processor. When the analysis chamber receives water from the swimming pool filtration circuit, the voltage from the generator is also a function of the quantity of water treated per unit time. The turbine and the electric generator are thus used as a water flow rate sensor.

In general, the voltage delivered by an electric generator, whether it is an alternator, a dynamo or another comparable rotating machine, is a function of the rotation speed of the shaft. To the first approximation, it is a proportionality function.

It should be specified that instead of the voltage delivered by the generator, it is also possible to measure current delivered by the generator, or a proportional branch current, by applying a signal proportional to the current or the voltage from the electric generator to the measurement input of the data processor. In the present description, the mention of the voltage from the generator is therefore understood as not excluding the possible use of another magnitude proportional to the rotation speed of the turbine as input signal to the data processor. As an example, the electric generator may be equipped with a return counter that detects a magnet or by any other system with which to detect the rotation speed of the turbine, and with which to generate a signal intended for the data processor.

The data processor may be a digital processor such as a microprocessor or a microcontroller. According to an advantageous embodiment of the analysis device, the data processor may be equipped with a radio wave transmitter-receiver housed in the sealed case and configured for transmitting at least one among the analysis data, command data and alert data.

With the transmitter-receiver, the data are sent by radio wave. It is considered that the data are transmitted by radio wave when they are transmitted wirelessly, by electromagnetic waves, and without assumption about the frequency of the waves. The transmitter-receiver is, for example, a radio frequency transmitter-receiver. Data can be sent from the data processor to external equipment. Data can also be received by the data processing from external equipment.

"Analysis data" are understood to mean data representative of physical-chemical properties of the water or representative of the sanitary quality of the water. These data may include values for temperature, flow rate, pressure, pH (potential hydrogen), ORP (oxidation-reduction potential), salinity, turbidity, etc.

"Command data" are understood to be data developed by the data processor and which could be received by equipment external to the analysis device in order to execute operations connected with maintaining the quality of the swimming pool water. This equipment may comprise a unit for processing water with ultraviolet radiation, a salt electrolysis system, metering pumps for injecting corrective additives into the swimming pool water, but also circulating pumps or valves. Together these equipment may be controlled and driven as a function of the physical-chemical properties of the water measured by the probes, but also as a function of the flow rate of the filtration circuit established from the rotation speed of the turbine and/or the voltage delivered by the electric generator.

"Alert data" are understood to be data which can be used for triggering an alarm system, visible or audible, or even daily which could be issued in message form to one or more remote communication devices. Alert data are issued where the processor detects an excursion outside predefined and stored range settings in one or more analysis data. Several radio communication modes between the analysis device and the external equipment may be provided. Communications may be established by radio frequency link with equipment in a swimming pool equipment room comprising pumps, treatment or heating devices, valves or the aforementioned metering pumps. In this case, the data processor may issue commands or values for driving this equipment. Beyond the analysis data and the command data, the processor may also send data for information about the state of the analysis device. It involves, for example, information about the operation of the data processor or the state of charge of the battery.

The analysis device may also be equipped with a Wi-Fi, Bluetooth or low-power wide area network (LPWAN) communication module. This serves to establish communication between the data processor and equipment such as a personal computer, tablet, smart phone or connected object for displaying analysis data. The analysis device may also use this communication for sending its operation data and measured values to an Internet server, with which to then allow creation of a history of measured values. Finally, the communication network may serve for sending alerts to a system user, and to do this even if the user is not using their personal computer, tablet or smart phone during appearance of an alert. An alert may be issued by sending a notice to a user device, by sending SMS, by sending email, or any other message type.

According to another possibility, not exclusive of the preceding, the data processor may also be equipped with an interface for output to the switches. Such an interface, designed for possible wired equipment connection, may comprise, for example, one or more electromechanical or static relays, whose switching state is driven by the data processor.

According to another possibility, not exclusive of the preceding, the data processor may be equipped with an input interface designed for a wired connection from an external probe or sensor capable of delivering a signal applied to the input of the data processor for adding to the "analysis data" and possibly being sent by radio wave to external equipment.

The invention also relates to a swimming pool comprising a filtration circuit provided with a circulating pump and at least one filter. Conforming to the invention, the filtration circuit is further provided with an analysis device such as previously described.

The term "swimming pool" is understood as encompassing private or public pools, but also hot tubs.

The analysis device takes advantage of the water flow caused by the circulating pump in the filtration circuit in order to drive the movement to the turbine and generate the energy necessary for the operation of the turbine.

The placement of an analysis device in the existing filtration circuit of a swimming pool does not require any electrical connection but simply a fluid connection, such that all or part of the water from the filtration circuit passes through the analysis chamber.

[Preferably, the analysis device may be connected downstream from the filter. This measure serves to avoid possible particles, which could be retained by the filter, from clogging the analysis chamber or interfering with the movement of the turbine.

Further, the analysis device may advantageously be connected in series with the circulating pump and the filter, with a water inlet and a water outlet of the analysis chamber connected to a pipe of the filtration circuit.

In this case, the analysis device also constitutes a witness to the proper operation of the filtration circuit. The possible failure of the circulating pump or dogging of the filter would be seen as a reduction or interruption of the flow of water through the analysis chamber and therefore a reduction or elimination of the rotation speed of the turbine.

The rotation speed of the turbine is established and monitored by the data processor receiving voltage data from the electric generator at the input thereof. It can be compared to a setting value or range stored in memory. The rotation speed of the turbine, indicative of the water flow through the analysis chamber, may also be used as a correction factor for other physical-chemical magnitudes established for the analysis of the water.

A connection of the analysis device on a branch of the filtration circuit is also conceivable.

As previously brought up, the swimming pool may further comprise at least one metering pump for corrective liquid. The metering pump may be driven as a function of at least one item of analysis data prepared by the data processor.

The metering pump may be driven either directly by the data processor, or via a driver unit external to the analysis device, which receives analysis data prepared by the data processor and sets an amount of corrective liquid as a function of this data. The driver unit is, for example, an electric supply for the metering pump in radio communication with the analysis device.

Other characteristics and advantages of the invention will emerge from the following description made with reference to the figures from the drawings. This description is given for illustration and is nonlimiting.

BRIEF DESCRIPTION OF THE DRAWINGS

The scale in the figures is arbitrary.

DETAILED DESCRIPTION OF THE INVENTION

In the following description, identical, similar or equivalent parts are referenced with the same reference signs so as to be able to relate one figure to another.

Figure 1:
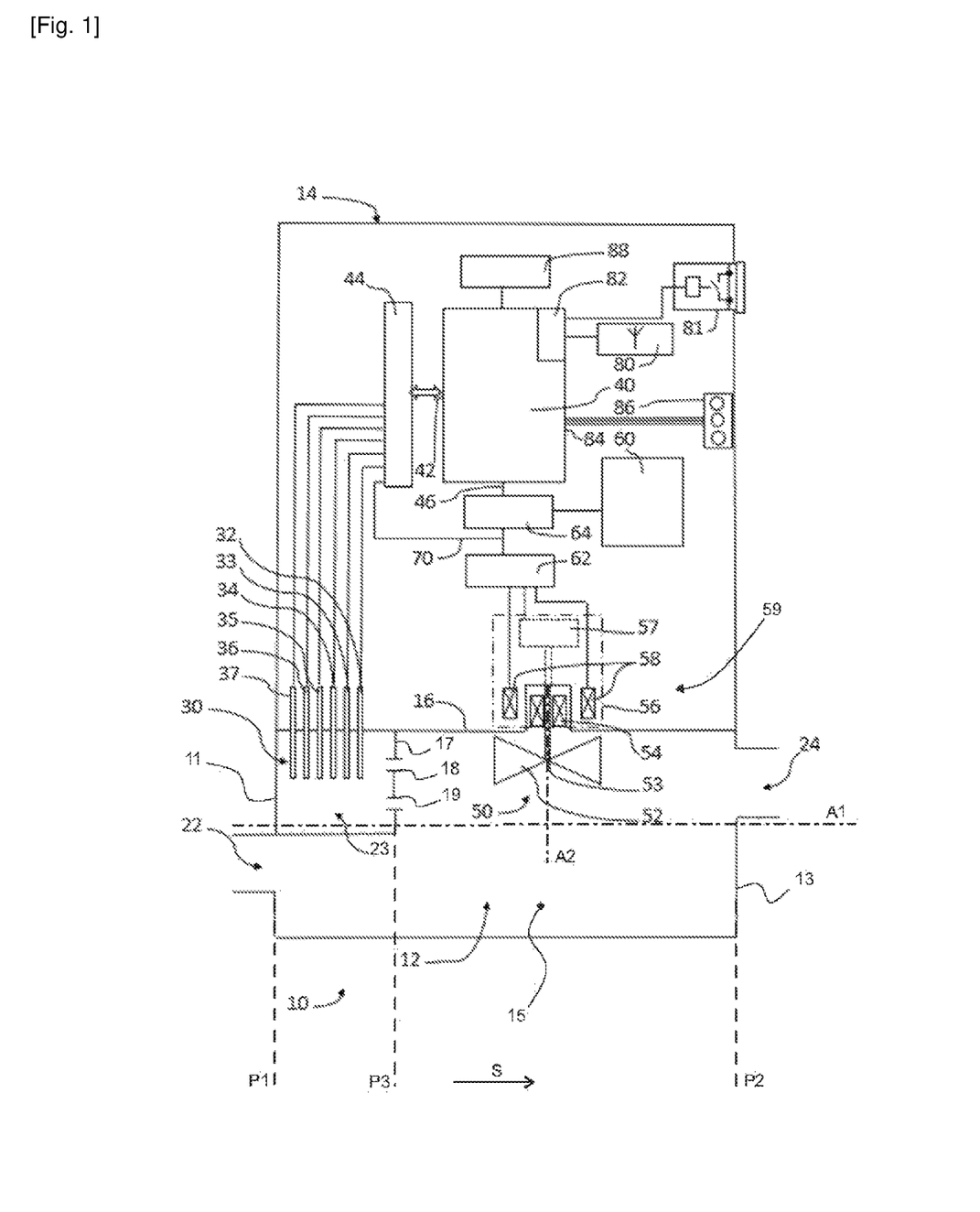
FIG. 1 is a simplified schematic representation of an analysis device according to the invention.

FIG. 1 shows schematically an analysis device 10 conforming to the invention. It comprises an analysis chamber 12, seen in section, and a sealed case 14 housing electrical and electronic components. The analysis chamber 12 is separated from the sealed case 14 by a partition 16.

The overall shape of the analysis chamber 12 is a cylinder with an axis of revolution A1, which forms a general axis of extension of the analysis chamber 12. The sealed case 14 overhangs the analysis chamber 12. In other words, the electrical and electronic components of the analysis device 10 are gathered inside a single sealed case 14 which adjoins the analysis chamber 12. In other words, again, the analysis chamber 12 and the sealed case 14 are contiguous with each other while being separated from each other by a single partition 16.

The analysis chamber 12 has a water inlet 22 and a water outlet 24 which could be connected to a water pipe.

The water inlet 22 is arranged through a first wall 11 delimiting the analysis chamber 12 and the water outlet 24 is arranged through a second wall 13 delimiting the analysis chamber 12. The first wall 11 and the second wall 13 are arranged across from each other and intersect the axis of revolution A1. More specifically, the first wall 11 extends inside of a first plane P1 and the second wall 13 extends inside of a second plane P2, where the first plane P1 and the second plane P2 are substantially orthogonal to the axis of revolution A1. These arrangements are such that the analysis chamber 12 could be traversed by a fluid 15, notably water or the like, along the flow direction S of the fluid 15 which is substantially parallel to the axis of revolution A1. Note that according to an implementation variant, the water inlet 22 could occupy the entire surface of the first wall 11 seen in the first plane P1, and that the water outlet 22 could occupy the entire surface of the second wall 13 seen in the second plane P2.

A set of probes 30 extends in the analysis chamber 12. The set of probes 30 comprises a temperature probe 32, a pH probe 33, an oxidation-reduction potential probe 34, and a salinity probe 35. The set of probes 30 could be supplemented by a dissolved solids probe 36 and a turbidity probe 37.

It can be seen that the probes 30 are housed in compartment 23 of the analysis chamber 12, communicating with the analysis chamber 12. The purpose of compartment 23 is to reduce the flow rate of the water passing through the analysis chamber 12 in the area of the probes 30 in order to avoid disruption of the measurements by a flow rate that is too high.

For this purpose, the compartment 23 is for example radially interposed between the water inlet 21 and the partition 16 which delimits the analysis chamber 12 from the sealed case 14. According to an embodiment, the compartment 23 is delimited by the first wall 11, the partition 16 and at least one third wall 17. The third wall 17 comprises a water admission opening 18 and a water evacuation opening 19 through which the water 15 is able to pass. The third wall 17 extends at least partially inside a third plane P3 which is interposed between the first plane P1 and the second plane P2 and which is orthogonal to the axis of revolution A1.

Together the probes from the set of probes 30 are connected to a data input 42 of the data processor 40. They are connected to it through an interface 44 configured for conditioning the analog signal and/or converting the analog signal from the probes 30 into a digital signal compatible with the data input 42 of the data processor 40. The interface 44 also serves to supply electric energy as needed to the active probes such as conductivity or turbidity measurement probes.

A turbine 50 is also located in the analysis chamber 12 and is provided with a propeller 52 and rotated by a flow of water 15 which could circulate through the analysis chamber 12 from the water inlet 22 thereof towards the water outlet 24 thereof. The propeller 52 is mobile on itself in rotation around a rotational axis A2 which is substantially orthogonal to the axis of revolution A1 and therefore to the flow direction S of the water 15 between the water inlet 22 in the water outlet 24. It follows from this that the speed of rotation of the propeller 52 is proportional to a speed of flow of the water 15 inside the analysis chamber 12 and therefore precisely representative of the speed of flow of the water 15 inside the analysis chamber 12. Note that the propeller 52 is for example arranged axially inside the analysis chamber 12 between the compartment 23 and the water outlet 24.

These arrangements are such that the losses of pressure affecting the water which circulates inside the analysis chamber are advantageously minimized.

The turbine 50 is equipped with permanent magnets which form the inductor 54 of an electric generator 56. The permanent magnets are secured to a rotor of the turbine 50 arranged in the analysis chamber 12. In FIG. 1, and for simplification, the permanent magnets are shown symbolically on a shaft 53 of the turbine 50 which extends along the axis of rotation A2. The electric generator 56 also comprises an armature 58 arranged inside the sealed case 14. The armature 58 is formed, for example, by one or more electric coils. In that way, a stator of the turbine 50 is arranged in the sealed case 14 whereas the rotor of the turbine 50 is immersed in the analysis chamber 12. The armature 58 and the inductor 54 of the electric generator 56 are magnetically coupled through the sealed wall 16 and form an alternator 59. In that way, a rotation of the turbine 50 and therefore of the inductor 54 causes the movement of an electric current in the armature 58. According to this embodiment, the shaft 53 of the turbine 50 does not pass through the partition 16 separating the analysis chamber 12 from the sealed case 14, such that no turning shaft seal is necessary. These arrangements guarantee a perfect and durable watertightness between the analysis chamber 12 and the sealed case 14.

According to a variant shown in dashed lines, the alternator 59 of the electric generator 56, essentially made up by the inductor 54 and the armature 58, may be replaced by a dynamo 57 mounted on an extension of the shaft 53 of the turbine 50. In this embodiment, the shaft 53 of the turbine passes through the partition 16 separating the analysis chamber 12 from the sealed case 14. A shaft seal, not shown, is provided.

The electric generator 56 is connected to an electric supply input of the data processor 40 via a rectifier 62 and a DC-DC voltage converter 64, providing for the delivery of a supply voltage suited to the data processor 40.

A battery 60 is also connected to the voltage converter 64 for supplying the data processor 40.

An electric current may pass through the electric generator 56 or the battery 60 towards the data processor 40 when the data processor 40 is supplied by the electric generator 56 or the battery 60, respectively. A current may also circulate through the electric generator 56 to the battery 60 for charging the battery 60.

The supply current and voltage for the data processor 40 are regulated by the voltage converter 64. Similarly, the charging current and voltage for the battery 60 are regulated by the voltage converter 64.

As already indicated, the battery 60 serves to supplement a temporary deficiency of energy produced by the electric generator 56 when the turbine 50 is not driven. This serves to guarantee the continuity of operation of the data processor 40 without an electrical connection outside the analysis device 10 being necessary, and without any human intervention such as replacing or recharging a battery.

In FIG. 1, an electrical connection 70 connecting the generator 56 to the data input 42 of the data processor 40 should be noted. The electrical connection 70 is done through a rectifier 62 and through the interface 44 of the data processor 40.

The rectified voltage available at the output of the rectifier 62 depends on the voltage delivered by the electric generator 56. It is proportional to the rotation speed of the turbine 50 and therefore to the flow of water 15 which passes through the analysis chamber 12. The use of this voltage by the data processing 40 allows the data processing 40 not only to monitor the operation of turbine 50, but also to measure the treated water flow, and to act on these parameters for the preparation of management commands for the swimming pool water.

Among the data prepared by the data processor 40, analysis data, alert data and command data can be distinguished. The analysis data, or the alert data, give information about the physical-chemical properties of the water or the sanitary quality of the water which passes through the analysis chamber 12. They may be sent to water quality monitoring or display equipment. Command data are data intended for equipment governing management of the swim pool water. This equipment, not shown in FIG. 1, may comprise, for example a water heater, a UV radiation source, a salt electrolysis system, metering pumps for swimming pool water correcting agents, one or more pumps for a swimming pool water filtration circuit and one or more solenoid valves. Such equipment is described with reference to FIG. 2.

Returning to FIG. 1, the analysis data, alert data and command data are transmitted towards the receiving equipment by radio wave. In that way, no wired connection is necessary between the analysis device 10 and this equipment. The radio link is provided by a radiofrequency transmitter-receiver 80 connected to a universal synchronous/asynchronous receiver-transmitter (USART) terminal 82 of the data processor 40. The radiofrequency transmitter-receiver is supplied with energy by the electric generator 56 or by the battery.

Another data output 84 of the data processor 40 is used to command a lighting device 86 whose color changes according to the analysis data of the water sanitary quality. The lighting device 86 comprises three different color light emitting diodes which, by combining colors, serve to produce various resulting colors indicating the water quality. The lighting device 86 may also be used for displaying failures, alerts relating to the sanitary quality of the water and/or the internal operation of the analysis device.

In the implementation example from FIG. 1, the lighting device 86 is arranged inside the sealed case 14 and the emitted light is visible through a transparent or translucent wall of the sealed case 14. Just the same, the lighting device 86 may also be outside the sealed case 14 and driven remotely by radio wave or even be arranged such that the emitted light is visible through the analysis chamber 12.

For this purpose, the analysis chamber 12 is in particular made of a transparent material, in particular transparent plastic, to allow a visual check of the turbidity of the water. In fact, the lighting device 86 housed in the sealed case 14 illuminates the analysis chamber 12 through the partition 16, also transparent, and changes the color of the water present in the analysis chamber 12 based on the measurements done and/or the state of the analysis device 10.

Reference 88 indicates a programmable memory associated with the data processor 40. It serves to program various analysis tasks or to control the data processor 40. It also serves to store setting values or ranges for water parameters that could be analyzed.

Memory, the analog-digital converters, the transmitter-receiver and the data processor may be independent components or may be integrated into a single package in the form of a dedicated microcontroller.

Reference 81 indicates an input-output interface. At the output, it may be equipped with electromechanical switches or static semiconductor switches to which swimming pool equipment can be connected as needed. Connection is understood as a wired connection by means of a suitable sealed connector.

Reference 81 may also be an input allowing attachment of an external probe or sensor capable of delivering a signal applied to the input of the data processor for adding "analysis data" and possibly being sent by radio wave to external equipment.

Figure 2:
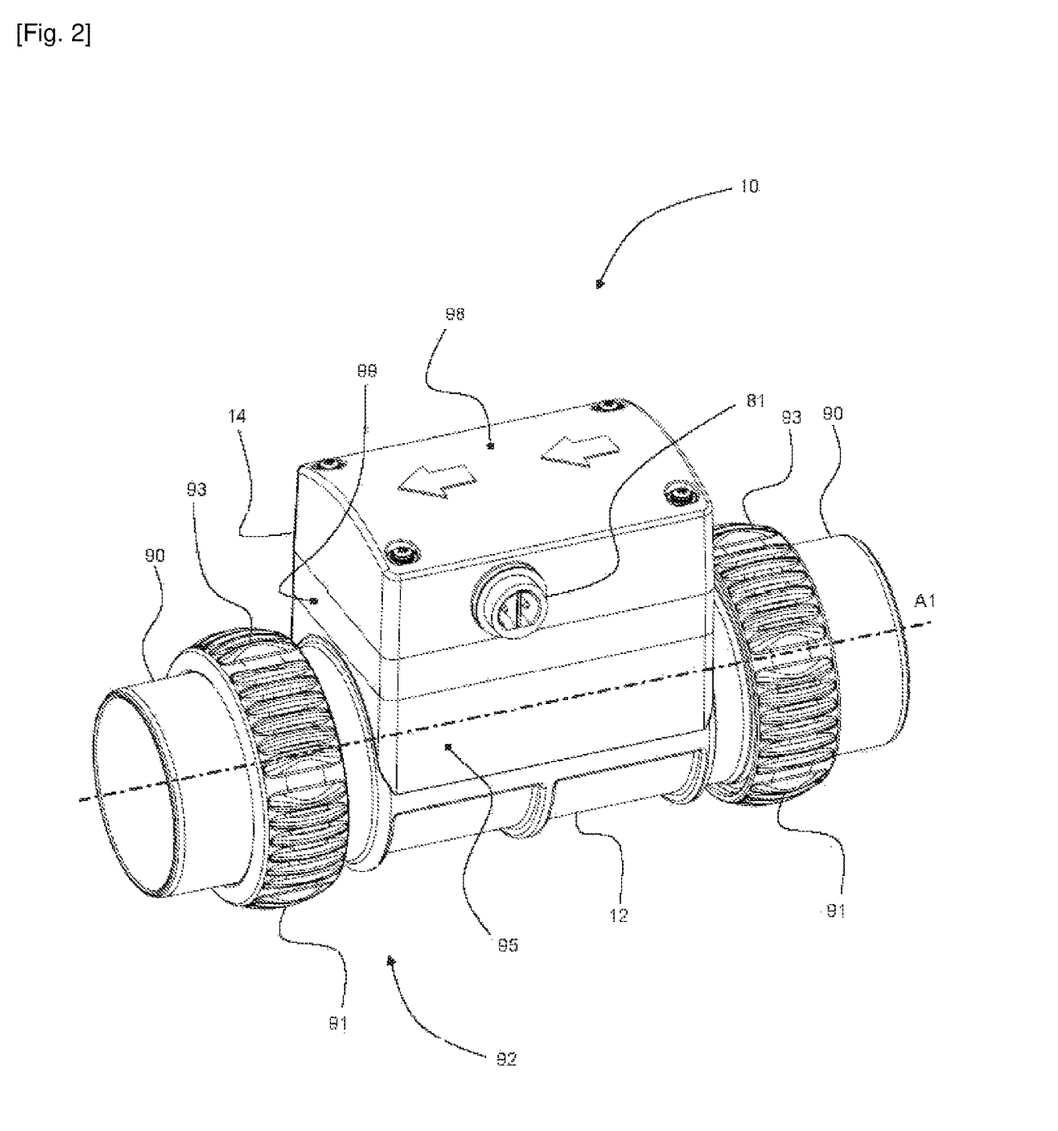
FIG. 2 is a perspective view of the analysis device shown in FIG. 1.
Figure 5:
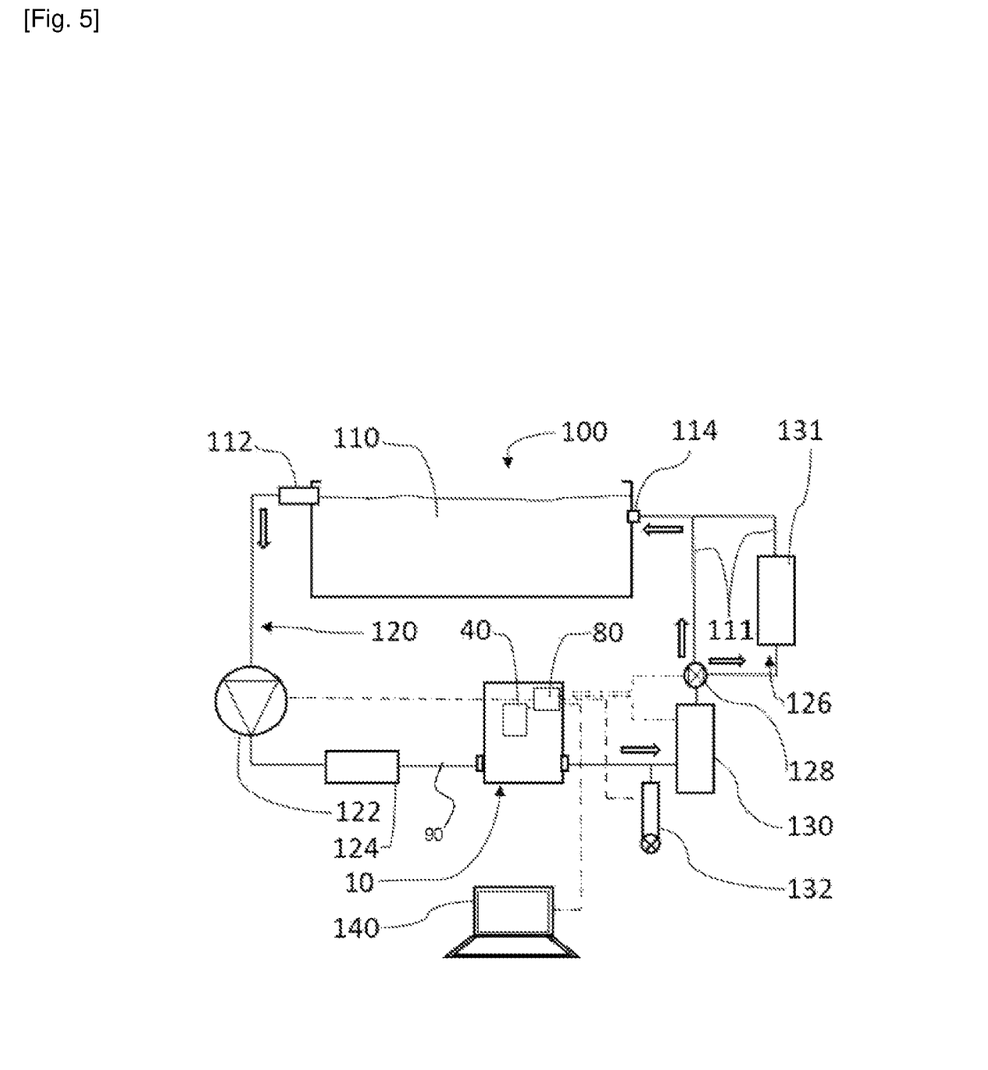
FIG. 5 is a simplified schematic representation of a swimming pool provided with a filtration circuit and an analysis device according to the invention.

On FIG. 2, the analysis device 10 is installed on a pipe 90 making up a swimming pool water filtration circuit shown in FIG. 5. For this purpose, the analysis device 10 comprises two annular flanges 91 which make up a device for connection 92 of the analysis device 10 onto the pipe 90. Each annular flange 91 is for example provided with relief 93 improving hold of the annular flange 91 onto the connection of the analysis device 10 on the pipe 90. Such a connection is in particular obtained by a rotation of each annular flange 91 about itself around an axis of revolution A1 for joining the threading of the annular flange 91 on complementary threading 93 arranged on the pipe 90 and on each axial end 94 of the analysis chamber 12 such as shown in FIG. 3.

Figure 3:
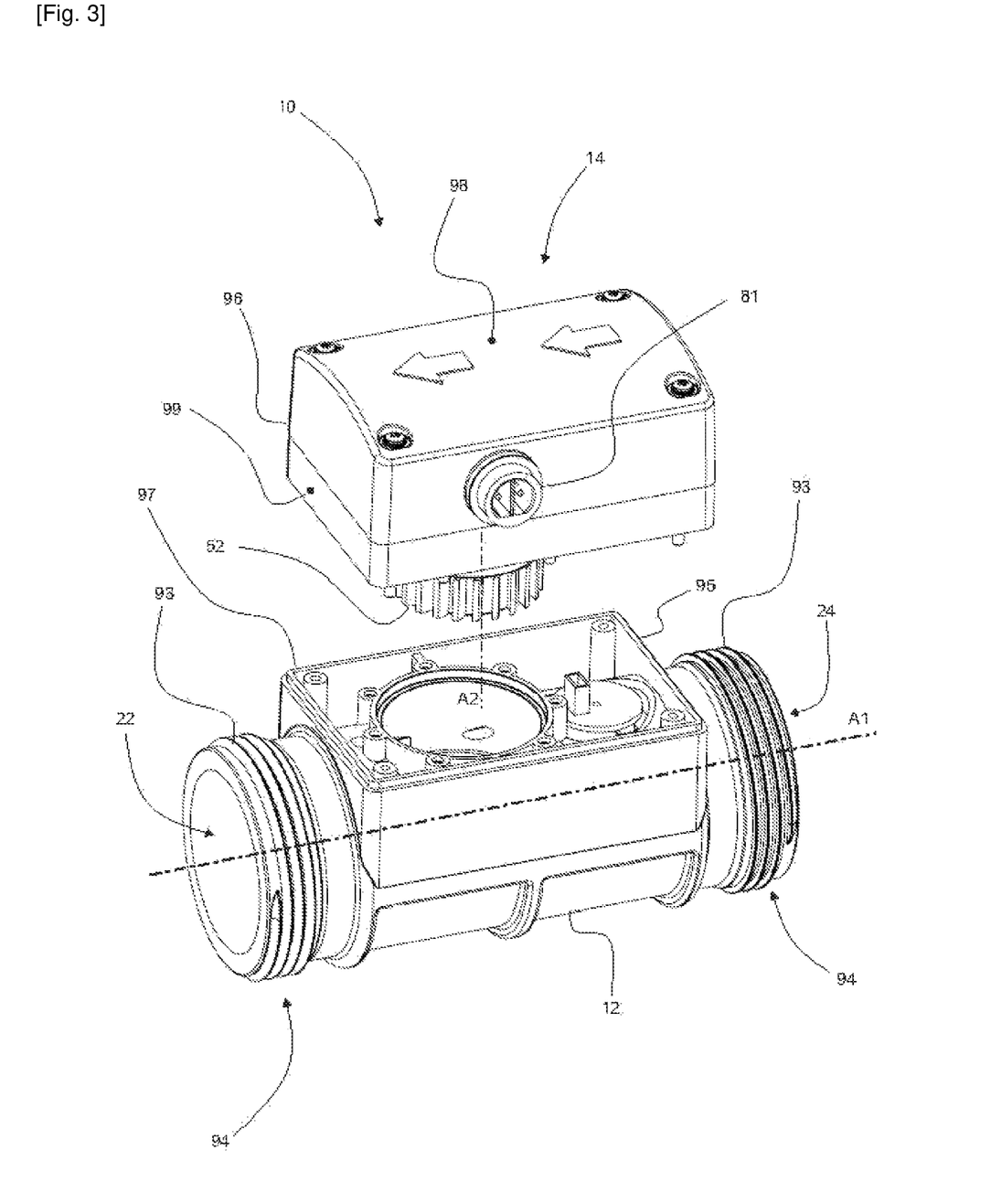
FIG. 3 is an exploded view with the analysis device shown in FIGS. 1 and 2.

In FIG. 3, the sealed case 14 comprises a base 95 secured to the analysis chamber 12 and a cover 96 returnable onto the base 95 via a flat seal 97. Note that the flat seal 97 extends for example inside a plane orthogonal to the axis of rotation A2 of the propeller 52 of the turbine 50.

Figure 4:
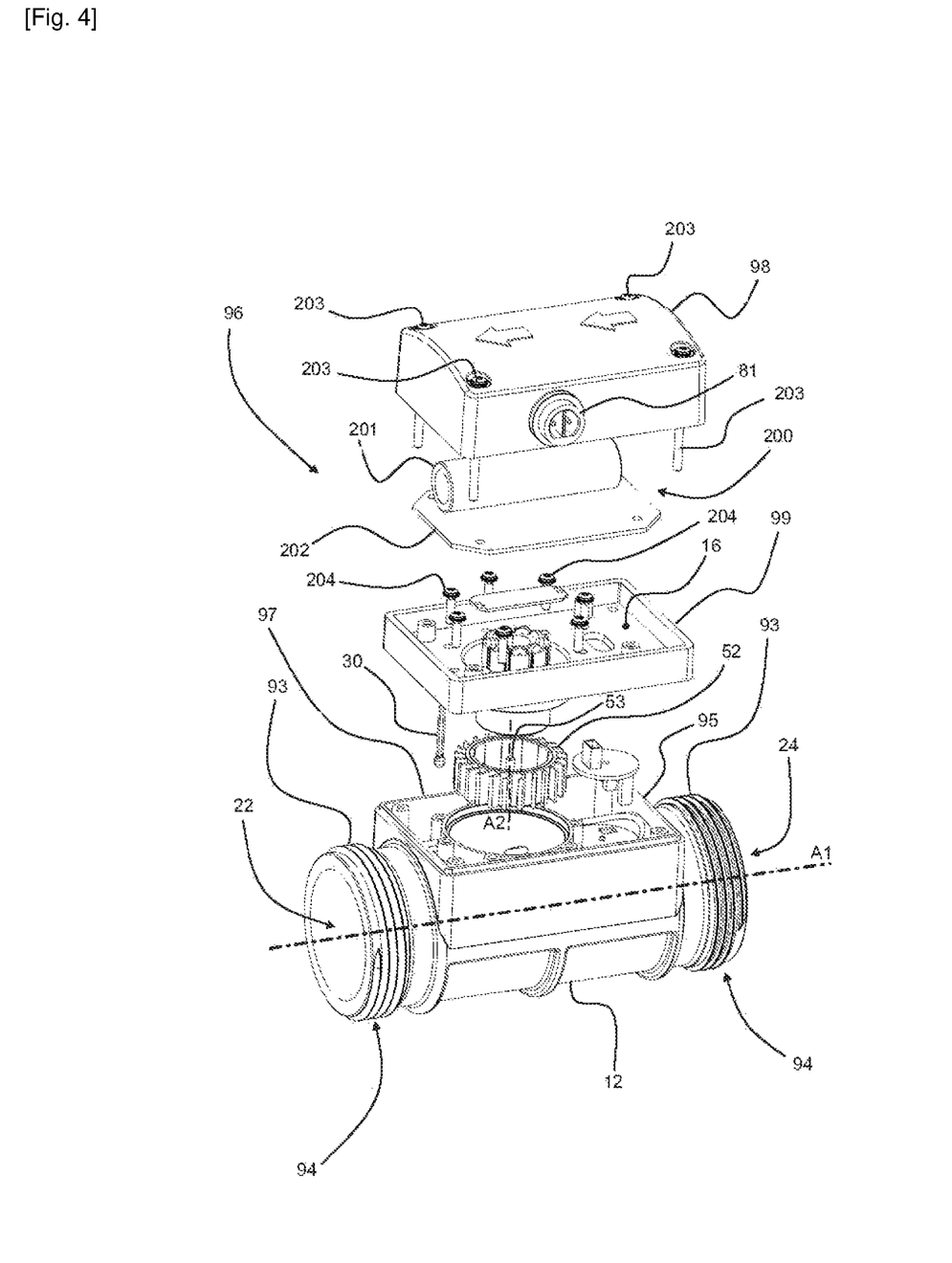
FIG. 4 is another exploded view of the analysis device shown in FIGS. 1 to 3.

In FIG. 4, the cover 96 comprises a lid 98 and the connecting part 99 where the connecting part 99 is placed in between the lid 98 and the base 95. The connecting part 99 is equipped with a sealed partition 16. The connecting part 99 delimits with the lid 98 an internal volume 200 suited for housing electrical and/or electronic components 201, in particular laid out on a circuit board 202. The lid 98 is brought on the connecting part 99 via first screwing means 203 or the like. Connecting part 99 is also brought onto the base by means of second screwing means 204.

FIG. 5 schematically shows a swimming pool 100 equipped with analysis device 10 conforming to the invention.

The swimming pool 100 comprises a pool 110 provided with a skimmer 112 and a filtration circuit 120 connecting the skimmer 112 to a return nozzle 114.

In sequence from the skimmer 112, the filtration circuit 120 comprises a circulating pump 122, a filter 124, the analysis device 10 such as previously described, and a water treatment unit 130. The analysis device 10 is placed between the filter 124 and the return nozzle 114. The various members are connected to each other by water pipes 111. The water pipes 111, shown symbolically, are formed of tubes and channels. The circulation of the water is shown by small arrows near the water pipes.

The water processing unit 130 may comprise, for example, an ultraviolet radiation source and/or an electrolysis cell.

Further, a branch 126 of the filtration circuit 120 comprises a valve 128 and a heating unit 131 for reheating the water. The heating unit 131 may be an exchanger for a boiler or a circulating solar panel, for example.

In the implementation example from FIG. 5, the valve 128 is a three-way motorized valve, driven by the analysis device 10. It serves to redirect, or not, all or part of the water from the filtration circuit 120 for reheating. The proportion of water circulating in the branch is controlled, for example, according to a temperature of the water established by the temperature probe 32 shown in FIG. 1.

A metering pump 132 is connected to a pipe of the filtration circuit 120. The metering pump 132 is configured for adding to the water as needed an additive intended to correct the chemical composition thereof. Several metering pumps can be installed according to the same plan for adding several different additives.

Reference 140 designates a remote portable computer, or other comparable communication equipment, connected to the analysis device 10 through a wireless communication network, for example the Internet, or to a local short-range network (Wi-Fi, Bluetooth, LPWAN). The analysis or alert data prepared by the data processor 40 of the analysis device 10 are transferred to the portable computer 140 or comparable communication equipment. They may be displayed and viewed by means of the dedicated graphical interface.

Further, various equipment of the filtration circuit, and in particular the circulating pump 122, valve 128, water treatment unit 130, and the metering pump 132 receive command data from the data processor 40 of the analysis device. These data are also sent wirelessly from the analysis device to the remote receiver, by means of the radiofrequency transmitter-receiver 80. The radio link between the analysis device 10 and the various equipment communicating with the analysis device 10 is shown symbolically by dashed lines. For simplification, only the data processor 40 and the transmitter-receiver 80 of the analysis device 10 are shown in FIG. 2.

The command data may be sent directly to the various equipment of the filtration circuit 120 by the analysis device 10. This assumes that each piece of equipment has a data transmitter-receiver and interface with which to drive operation thereof in response to the command data prepared by the data processor of the analysis device. According to another possibility, the command data may also be sent to a driving interface shared by the various equipment. This interface may be arranged near the equipment in a swimming pool equipment room, not shown. In the latter case, the equipment in the filtration circuit may be connected to the shared driving interface by wired connection.

The control data prepared by the data processor 40 may be proportional to the water flow in the filtration circuit or may be conditional on the existence of a water flow in this circuit. The existence of the water flow or the size of the water flow is measured by the signal coming from the electric generator in the way previously described with reference to FIG. 1.

For illustration, injection of pH correcting liquid in the water pipes is not desirable when the water is not circulating, in order to avoid accumulation of products that could act aggressively on the walls of the water pipes 111.

Also, when the data processor 40 detects that there is no water flowing, characterized by a zero-output voltage from the electric generator, a command inhibiting operation of the metering pump 132 may be issued.

According to an implementation variant, the water analysis device 10 may be configured in the form of an insert, which can be housed, in particular screwed, into the return nozzle 114 of the pool. In this case, the water inlet 22 and the water outlet 24 of the analysis chamber 12 of the water analysis device are preferably coaxial, in the extension of each other and centered on an axis of the return nozzle. The water from the return nozzle passing the analysis device then serves to drive the turbine of the device. Such an embodiment allows a simple installation of the water analysis device in an existing pool, and, because it is autonomous, does not require any electrical cabling.

These arrangements are such that the analysis device 10 uses hydraulic energy both for supplying energy and for storing the energy necessary for operating independently for several hours without water circulation within the filtration circuit 120. Such circumstances could happen when the filter 124 is fouled or when an object of any kind blocks the filtration circuit 120.

It is understood that the turbine 50 actuates the dynamo 57 or an alternator 59 which converts the pressure of the water moving in the filtration circuit 120 into electric energy. The dynamo 57 delivers a direct voltage directly, whereas the alternator 59 provides a three-phase voltage which must be rectified. In both cases, the energy supplied is proportional to the speed of the circulating water and therefore the flow rate of water in the filtration circuit 120. Other than the production of energy, the turbine 50 therefore also serves to detect the absence of flow rate or of filter failures (clogging of the filter, blocked skimmer, fouled pump, closed valve, etc.) and measure the flow rate of water passing through the analysis device 10.

The analysis device 10 calculates the water flow rate based on an electric voltage produced by the voltage converter 64 from the turbine 50. The electric voltage supplied is proportional to the rotation speed of the turbine 50 and therefore to the flow rate of water passing through the analysis device 10. The analysis device is therefore suited for measuring the water flow rate by monitoring the voltage provided by the voltage converter 64. This flow rate is crucial information for the proper operation of the swimming pool 110 and the detection or absence of this flow rate serves to know whether the circulating pump 122 is operating or stopped. This information is used by the analysis device 10 for its own management and is sent to a remote receiver which considers it for triggering, for example, chlorine production or else injection of a pH correcting liquid into the filtration circuit 120. It is in fact indispensable to be sure that water is circulating in the filtration circuit 120 to avoid any risk of accumulation of aggressive products in the filtration circuit 120.

Beyond detection of the flow rate, it is important to measure it in order to adjust the speed of the circulating pump 122 or to initiate washing of the filter 124. For example, it is generally accepted that a water circulation speed of around 1.5 m/s to 2 m/s is ideal for good filtration. In a pipe with a diameter of 50 mm, this corresponds to a flow rate of 14 m$^3$/h, which allows recycling of 56 M$^3$ swimming pool four times per day.

Fouling of the filter 124 increases of flow resistance and reduces the water flow rate in the filtration circuit 120. The flow rate information is sent to the receiver [and] may lead to an adjustment of the filtration rate and/or be compared to a minimum threshold and trigger a washing of the filter 124 or else a user alert.

The electric energy provided by the turbine 50 is used for charging a battery 60 which serves in part to stabilize the voltage supplied to the data processor 40 and to assure the autonomous operation of the analysis device even when water is not circulating inside the filtration circuit 120. In fact, the filtration may only operate for a few hours per day and the analysis device 10 must be able to send measurement values and in particular the water temperature when there is no filtration. Thus, the battery 60 has sufficient storage capacity to supply the operation of the analysis device 10 without circulation of water for about one day.

A circuit monitoring the charge on the battery 60 serves to adjust the electric consumption of the analysis device 10 as a function of the level of charge of the battery 60. In that way, when the charge level of the battery 60 is below preset thresholds, the device can reduce the brightness of the lighting device 86, reduce the measurement and radio transmissions frequency, alert the user by very short flashes of light, and send notifications to a portable telephone type receiver.

The invention claimed is:

1. A water analysis device comprising:
   an analysis chamber provided with at least one water inlet and at least one water outlet;
   a sealed case adjacent to the analysis chamber and isolated from the analysis chamber via a partition;
   a data processor housed in the sealed case;
   at least one probe, electrically connected to a data input of the data processor, and extending into the analysis chamber;
   an electric supply electrically connected to a supply inlet of the data processor, where the electric supply comprises an electric generator provided with a turbine housed in the analysis chamber, and where the electric generator delivers a signal that is a function of the rotation speed of the turbine and is electrically connected to the data input of the data processor for sending said signal to the data processor, where the turbine is provided with a propeller mobile on itself in rotation around a rotational axis which is orthogonal to an axis of revolution of the analysis chamber, where the probe is housed inside a compartment of the analysis chamber which is radially interposed between the water inlet and the partition, where the propeller is arranged axially inside the analysis chamber between the compartment and the water outlet.

2. The analysis device according to claim 1, wherein the electric generator comprises one of an alternator and a dynamo.

3. The analysis device according to claim 2, wherein the turbine is provided with a shaft connecting the propeller to the dynamo or the alternator.

4. The analysis device according to claim 3, wherein the shaft of the turbine passes through the partition separating the analysis chamber from the sealed case.

5. The analysis device according to claim 3, wherein the electric generator comprises a permanent magnet inductor secured to the turbine and an armature housed in the sealed case.

6. The analysis device according to claim 1, wherein the operation signal for the turbine rotation speed is an output voltage from the electric generator.

7. The analysis device according to claim 1, wherein the electric supply further comprises an electric energy storage unit housed inside the sealed case.

8. The analysis device according to claim 1, wherein the data processor is equipped with a radio wave transmitter-receiver housed in the sealed case and configured for transmitting at least one among the analysis data, command data and alert data.

9. The analysis device according to claim 1, wherein the data processor is equipped with an external input-output interface.

10. The analysis device according to claim 1, wherein the probe is selected from a temperature probe, a pH probe, an oxidation-reduction potential probe, a salinity probe, a total dissolved solids probe, and a turbidity probe.

11. A swimming pool comprising a filtration circuit provided with a circulating pump and at least one filter, wherein the filtration circuit is additionally provided with an analysis device according to claim 1.

12. The swimming pool according to claim 11, wherein the analysis device is connected downstream from the filter.

13. The swimming pool according to claim 11, wherein the analysis device is connected in series with the circulating pump and the filter, with the water inlet and the water outlet of the analysis chamber connected to a pipe of the filtration circuit.

14. The swimming pool according to claim 11, further comprising at least one metering pump for corrective liquid.

* * * * *